(12) United States Patent
Voytenko

(10) Patent No.: US 9,325,179 B1
(45) Date of Patent: Apr. 26, 2016

(54) APPARATUS FOR GENERATING A VOLTAGE SURGE FROM LOW VOLTAGE BATTERIES THAT ARE CHARGED IN PARALLEL AND DISCHARGED IN SERIES

(71) Applicant: Rostislav Voytenko, Loveland, CO (US)

(72) Inventor: Rostislav Voytenko, Loveland, CO (US)

( * ) Notice: Subject to any disclaimer, the term of this patent is extended or adjusted under 35 U.S.C. 154(b) by 140 days.

(21) Appl. No.: 13/933,528

(22) Filed: Jul. 2, 2013

(51) Int. Cl.
*H02J 7/00* (2006.01)
*A61N 1/39* (2006.01)
*A61N 1/378* (2006.01)

(52) U.S. Cl.
CPC .............. *H02J 7/0024* (2013.01); *A61N 1/378* (2013.01); *A61N 1/3931* (2013.01); *A61N 1/3975* (2013.01)

(58) Field of Classification Search
CPC ....................................... H02J 7/0024
USPC ........................................... 320/117
See application file for complete search history.

(56) References Cited

U.S. PATENT DOCUMENTS

| | | | | |
|---|---|---|---|---|
| 3,576,383 | A * | 4/1971 | Fuller et al. | 431/255 |
| 3,579,074 | A * | 5/1971 | Richell | 320/166 |
| 3,589,003 | A | 6/1971 | Kastner | |
| 3,628,122 | A | 12/1971 | Rodewald | |
| 3,838,327 | A * | 9/1974 | Uemichi | H02J 7/1423 320/116 |
| 4,297,629 | A * | 10/1981 | Godard et al. | 320/117 |
| 5,121,046 | A * | 6/1992 | McCullough | 320/117 |
| 5,225,761 | A * | 7/1993 | Albright | 320/117 |
| 5,369,351 | A * | 11/1994 | Adams | 320/121 |
| 5,497,066 | A * | 3/1996 | Drouillard et al. | 320/117 |
| 5,621,255 | A | 4/1997 | Leon et al. | |
| 5,811,959 | A * | 9/1998 | Kejha | 320/126 |
| 5,825,155 | A * | 10/1998 | Ito et al. | 320/118 |
| 6,093,982 | A * | 7/2000 | Kroll | 307/115 |
| 6,175,214 | B1 * | 1/2001 | Mendoza et al. | 320/116 |
| 6,211,683 | B1 * | 4/2001 | Wolf | 324/548 |
| 6,310,789 | B1 * | 10/2001 | Nebrigic | H02J 7/0065 307/110 |
| 6,346,794 | B1 * | 2/2002 | Odaohhara | 320/116 |
| 7,499,293 | B2 | 3/2009 | Terazawa et al. | |
| 7,642,749 | B2 * | 1/2010 | Nishida | H02J 7/0024 320/107 |
| 7,728,554 | B2 | 6/2010 | Kim et al. | |
| 2002/0180276 | A1 | 12/2002 | Sakuma et al. | |

(Continued)

FOREIGN PATENT DOCUMENTS

| | | | |
|---|---|---|---|
| GB | 639023 | * | 6/1950 |
| JP | 55092580 | * | 7/1980 |
| JP | 57166887 | * | 10/1982 |

OTHER PUBLICATIONS

"Grounding in Portable Devices," Jackrae, Arduino Forums, Published Sep. 9, 2011, Accessed Online Nov. 5, 2015, http://forum.arduino.cc/index.php?topic=71803.0.*

*Primary Examiner* — Drew A Dunn
*Assistant Examiner* — John Trischler
(74) *Attorney, Agent, or Firm* — IP Law Leaders PLLC

(57) ABSTRACT

Apparatus for generating a voltage surge which can be in the form of a voltage pulse. More specifically, the invention is an apparatus in which low voltage sources charge in parallel and discharge in series to generate a voltage sufficient to drive devices such as, but not limited to, a solenoid. The low voltage sources can be rechargeable batteries such as, but not limited to, 1.5 V or 9 V batteries or a combination of different voltage rechargeable batteries. The apparatus comprises one or more modules in which a battery is directed to charge in parallel but discharge in series. The switch-over from charging to discharging is by means of transistors in each module that cause the modules to discharge in unison thereby creating a voltage surge which can be in the form of a voltage pulse.

3 Claims, 5 Drawing Sheets

(56) References Cited

U.S. PATENT DOCUMENTS

2004/0189250 A1* 9/2004 Nishida ............... H02J 7/0024
320/116

2010/0253154 A1* 10/2010 Yeates ................. H02M 3/07
307/110

2012/0299557 A1* 11/2012 Kwon ................. H02J 17/00
320/166

* cited by examiner

| TABLE 1 ||
|---|---|
| part # | Description |
| 100, 100a | circuit 100 and 100a, respectively |
| 120 | charger 120 |
| 140 | output 140 |
| 160 | diode D1 |
| 180 | diode D2 |
| 200 | module battery BT1 located in module 1000 |
| 220 | non-module battery BT2 |
| 240 | resistor R1 |
| 260 | transistor Q1 |
| 280 | transistor Q2 |
| 285 | module 285 |
| 300 | switch on/off 300 |
| 301 | controller 301 |
| 304 | adjustable pulse timer 304 |
| 305 | circuit 305 |
| 307 | module series 307 |
| 310 | transistor Q2 |
| 320 | transistor Q1 |
| 330 | transistor Q3 |
| 340 | battery BAT1 |
| 350 | diode 350 |
| 400 | control switch 400 |
| 405 | line 405 leading from control switch 400 |
| 410 | output 410 |
| 500 | diode 500 |
| 510 | non-module battery BAT2 |
| 1000 | module 1000 |
| 1100 | module 1100 |
| 1200 | module 1200 |

*FIG. 1*

TABLE 2
(Circuit 100)

| Switch 300 | Transistor Q1 260 | Transistor Q2 280 | Battery BT1 200 | Battery BT2 220 | Comments |
|---|---|---|---|---|---|
| On | Closed (*i.e.* OFF) | Open (*i.e.* ON) | Charging via D1 and Q2 | Charging via D2 | Batteries BT1 and BT2 charging in parallel |
| Off | Open (*i.e.* ON) | Closed (*i.e.* OFF) | Discharging | Discharging | Batteries BT1 and BT2 are in series; voltage delivered to Output 140 is double that of a single battery's output; D1 ensures output is directed to Output 140 |

*FIG. 3*

APPARATUS FOR GENERATING A VOLTAGE SURGE FROM LOW VOLTAGE BATTERIES THAT ARE CHARGED IN PARALLEL AND DISCHARGED IN SERIES

CROSS-REFERENCE TO RELATED APPLICATIONS

Not Applicable.

STATEMENT REGARDING FEDERALLY SPONSORED RESEARCH OR DEVELOPMENT

Not Applicable.

FIELD OF THE INVENTION

This invention relates to an apparatus for generating a voltage surge or pulse.

BACKGROUND OF THE INVENTION

U.S. Pat. No. 5,621,255 describes a Marx generator which includes a number of capacitors (E) connected in series via spark gaps (E), between two output terminals and a power supply circuit that charges the capacitors in parallel. The capacitors are connected in series by a flat line formed of two metal strips running parallel and facing one another. These strips are connected together electrically at one end of the line and respectively to the output terminals at the other end and consist of one continuous strip and a second strip subdivided by transverse slots into successive plane sections interconnected in series alternately by a capacitor and a surface spark gap.

United States Patent Application Number 20020180276 describes a simple and less expensive high voltage pulse generating circuit including a low voltage direct current voltage source having one output terminal connected to the other output terminal via a series circuit of a first switch with a low withstand voltage, an inductance storing a inductive energy and a second switch with a high withstand voltage, and a branch circuit including a free-wheel diode being connected between the other output terminal of the direct current voltage source and a common connection point between the first switch and the inductance. After storing inductive energy in the inductance by turning-on the first and second switches, these first and second switches are turned-off to commutate the energy stored in the inductance into a capacitive load connected across the second switch to charge the load abruptly and generate a high voltage pulse having a very narrow width without using a complicated and expensive magnetic compression circuit.

U.S. Pat. No. 3,628,122 describes a multistage Marx impulse generator circuit to which protective resistors are connected in series or in parallel with charging switches. The Ohmic value of the protective resistors is chosen so that in the case of premature flashover across a spark gap, the energy stored in the generator can be absorbed by the protective resistors.

None of the above inventions and patents, taken either singly or in combination, is seen to describe the instant invention as claimed.

SUMMARY OF THE INVENTION

An apparatus in the form of a circuit for generating a voltage surge or pulse. More specifically, the invention is an apparatus in which low voltage sources charge in parallel and discharge in series to generate a voltage surge sufficient to drive devices such as, but not limited to, a solenoid. The low voltage sources can be batteries such as, but not limited to, 9 volt batteries.

The circuit comprises modules arranged in series thereby defining a module series. During normal operation the module series defaults to charge mode connected to a charger. In discharge mode the module series is in series with a non-module battery to produce a voltage surge which can be in the form of a voltage pulse.

Each module comprises a module circuit which in turn comprises a module battery and an arrangement of transistors; the transistors in each module enable fast switching between charging and discharging of the module's battery. In non-discharge mode each module battery is set on charge, but in switching to discharge mode the transistors in each module direct voltage from the module's battery to the next module in the module series and finally to the non-module battery to produce an output in the form of a voltage surge which can be in the form of a voltage pulse. The switch-over from charging to discharging is performed by the transistors in each module circuit. Each module circuit is operably connected to a switch which causes each module to discharge in unison thereby creating a voltage surge which can be in the form of a voltage pulse.

BRIEF DESCRIPTION OF THE DRAWINGS

FIG. 1 shows a table (Table 1) that lists reference numbers and their associated descriptions.

FIG. 3 shows a logic table, according to the present invention.

Similar reference characters denote corresponding features consistently throughout the attached drawings.

DETAILED DESCRIPTION OF THE PREFERRED EMBODIMENTS

The invention is directed to an apparatus in which low voltage sources charge in parallel and discharge in series to generate, for example, a voltage sufficient to drive devices such as, but not limited to, a solenoid. The low voltage sources can be batteries such as, but not limited to, 9 volt batteries.

The invention comprises one or more modules in which a battery is directed to charge in parallel but discharge in series. The switch-over from charging to discharging is by means of transistors in each module that cause the modules to discharge in unison thereby creating a voltage surge or a pulse if, for example, a means for creating a voltage pulse is used such as an adjustable pulse timer. A summary of the component parts are listed in Table 1 (see FIG. 1).

Figure 2:
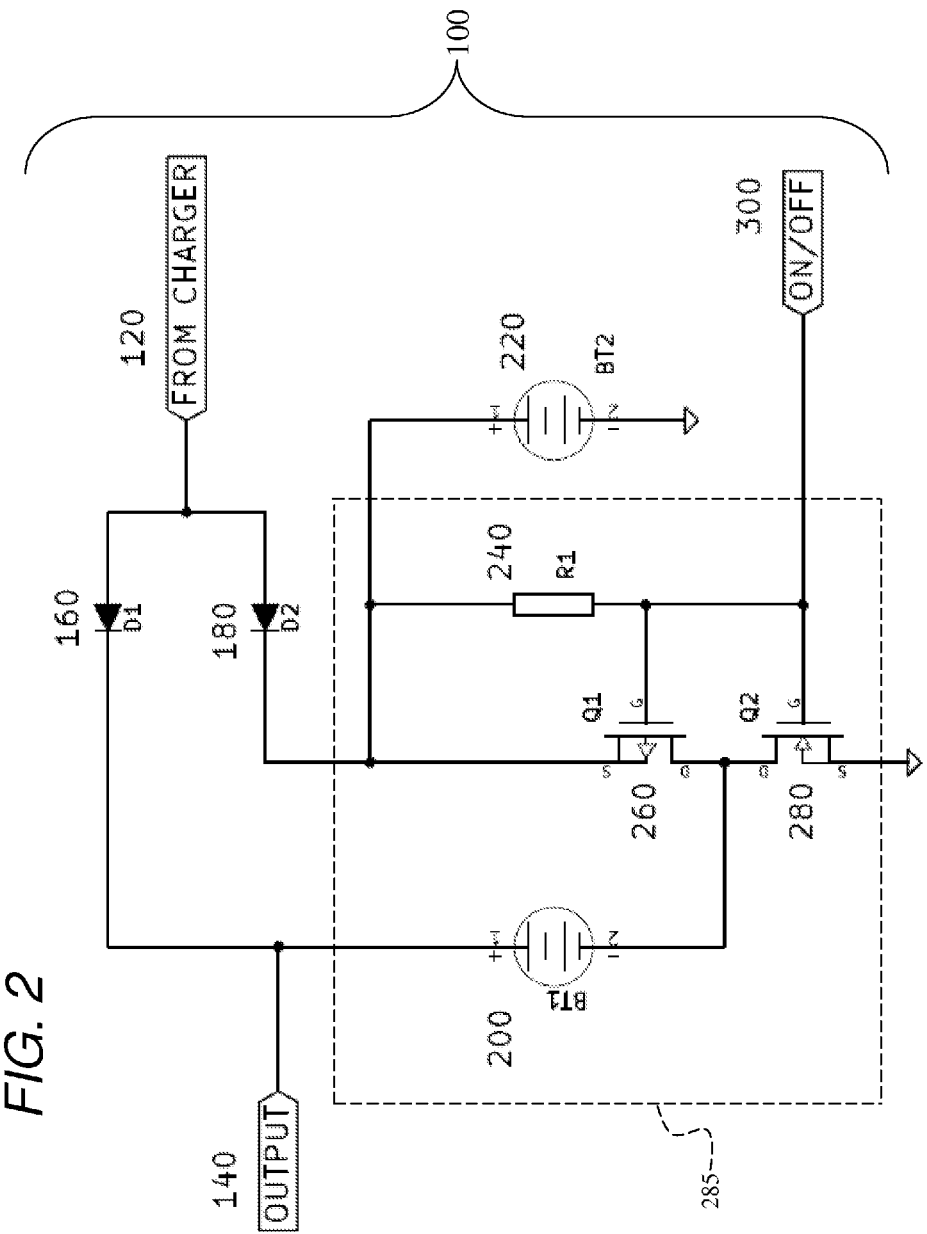
FIG. 2 shows a circuit, according to the present invention.

FIG. 2 is a circuit 100 which demonstrates the general principles of the invention. The circuit 100 is made up of a charger 120, an output 140, first and second diodes D1 and D2 (labeled as 160 and 180, respectively), batteries BT1 and BT2 (labeled as 200 and 220, respectively), a resistor 240, first transistor Q1 and second transistor Q2 (labeled as 260 and 280, respectively), and switch 300. Table 2 (FIG. 3) is a logic table that describes the operation of circuit 100 according to the present invention. Parts 200, 240, 260, and 280 make up a module 285 (shown as dashed-lines in FIG. 2). The circuit 100 can include a series of like modules to provide a desired voltage surge at output 140.

Figure 4:
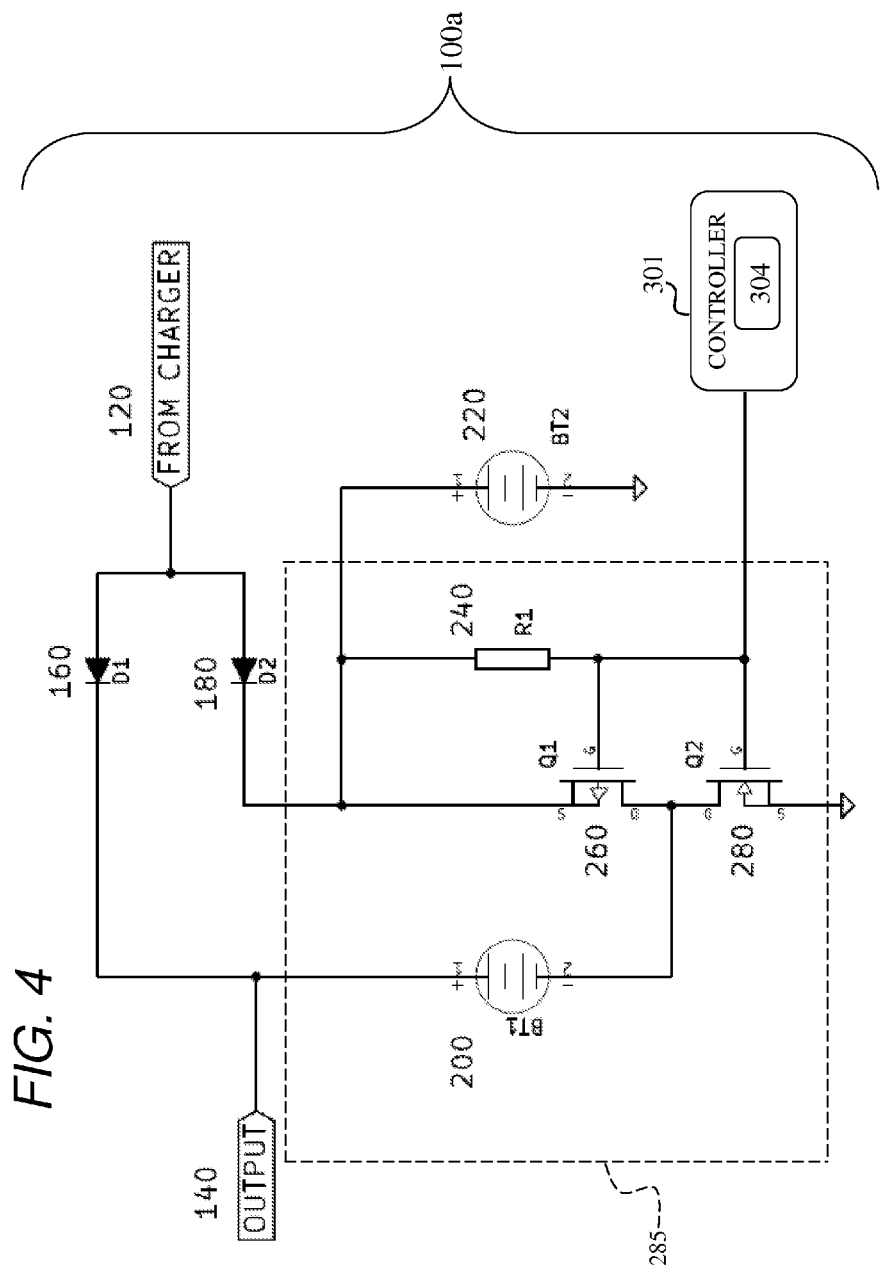
FIG. 4 shows a circuit, according to the present invention.

The switch 300 can be replaced by a controller 301 which includes an adjustable pulse timer 304 (see circuit 100a shown in FIG. 4). The terms "control" and "controller" are, for the purposes of this patent disclosure regarded as equivalent terms.

In one embodiment of the invention a circuit is provided having a plurality of modules in parallel branches but also coupled in series thereby defining a module series; a non-module battery is located in series with the module series. During normal operation the non-module battery and the modules that make up the module series default to charge mode. In discharge mode the module series is in series with the non-module battery to produce a voltage surge which can be in the form of a voltage pulse.

Each module comprises a module circuit which in turn comprises a module battery and an arrangement of transistors; the transistors in each module enable fast switching between charging and discharging of the module's battery. In non-discharge mode each the non-module battery and each module battery is set on charge, but in switching to discharge mode the non-module battery and module batteries in the module series act as a series of batteries directing a surge voltage to an output. The switch-over from charging to discharging is performed by the transistors in each module circuit. The non-module battery and module batteries discharge in unison and thereby generate a voltage surge.

Figure 5:
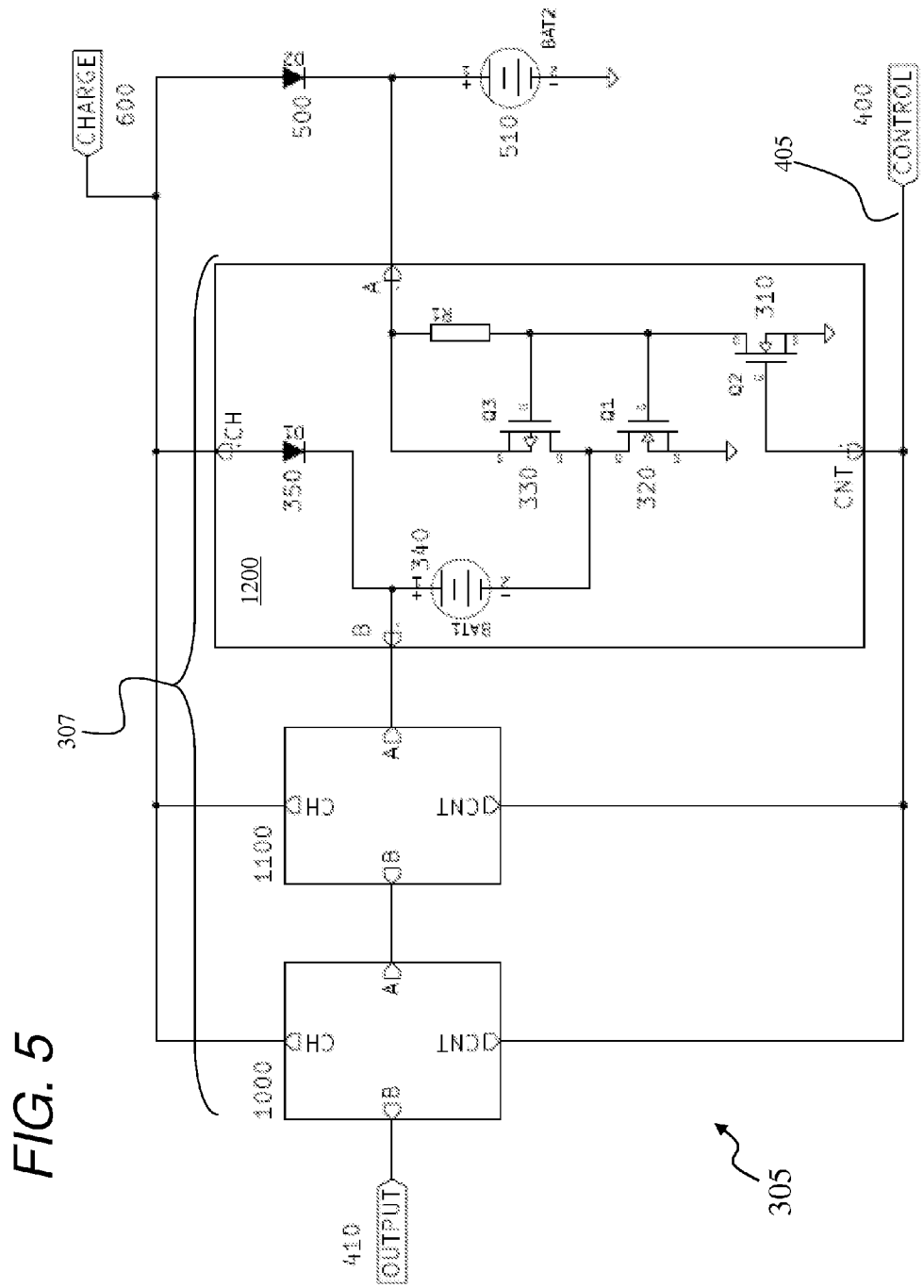
FIG. 5 shows a circuit, according to the present invention.

FIG. 5 shows a multi-modular circuit 305 for quadruple voltage output during ON state according to the invention. The circuit 305 comprises a plurality of modules 1000, 1100, and 1200 (labeled collectively as module series 307); the modules form parallel branches with respect to each other. The modules are also coupled in series for transferring voltage from one module to the next in the series 307 in the direction of the output 410. The internal schematic for module 1200 is shown; the internal schematic of modules 1000 and 1100 being the same as module 1200; further descriptions of the components found in circuit 305 is found in Table 1 (FIG. 1).

With respect to voltage delivery to output 410 modules 1000 and 1200 define nearest and furthest opposite ends of the module series 307, wherein module 1000 is electrically coupled to output 410, and module 1200 is electrically coupled to non-module battery BAT2 at 510. During discharge, voltage from non-module battery BAT2 at 510 is delivered to module 1200 via transistor Q3 at 330; the voltage from BAT2 at 510 is added to the voltage of the modules in the module series 307 and thence directed to output 410. It should be understood that circuit 305 ensures that the batteries in module series 307 and the non-modular battery BAT2 at 510 discharge in unison in response to inputs from control 400 to send a voltage surge to output 410.

While only three modules 1000, 1100, and 1200 are shown in circuit 305 it should be understood that the number of modules can be any number to achieve a desired voltage output at 410. The circuit 305 is significantly and patently distinct from prior art apparatus and methods that typically rely on capacitors such as those described in U.S. Pat. No. 3,628,122.

The circuit 305 has two states; an OFF state and an ON state which is set by adjusting control 400. In the OFF state the voltage output equals the voltage of the single battery BAT2 at 510 in circuit 305. In the ON state the output voltage (Vout) when the voltage of each battery in the modules 1000, 1100, and 1200 in circuit 305 is equal to $V_{510}$, where $V_{510}$ is the voltage of battery BAT2 at 510, whereupon Vout is:

$$Vout=V_{510}*(\text{number of modules}+1) \quad \text{Eq(i)}$$

$$\text{Otherwise } Vout=V_{510}+V_{1000}+V_{1100}+V_{1200} \quad \text{Eq(ii)}$$

$$\text{In general: } Vout=V_{510}+V1+V2+V3\ldots+Vn \quad \text{Eq(iii)}$$

Where in Eq(iii), n=the voltage of the last module in the series V1, V2 . . . Vn In more detail, in the OFF state the control line 405 voltage is LOW; transistor Q2 at 310 is OFF; transistor Q1 at 320 is ON; transistor Q3 at 330 is OFF. The battery BAT1 at 340 is charging from charge source 600 via diode D1 (350) and transistor Q1 (320) and thence to ground; each battery in the modules 1000 and 1100 are also charging. The main battery BAT2 at 510 is also being charged from charge source 600 via diode D2 (500).

In the ON state the control line 405 voltage is HIGH; transistor Q2 at 310 is ON; transistor Q1 at 320 is OFF; transistor Q3 at 330 is ON. The battery BAT1 at 340 is now connected between terminals A and B (and thence to the modular battery, not shown, in module 1100) and also connected in series with BAT2 at 510. The battery in module 1100 is also connected to the battery in module 1000, thus the non-modular battery 510 and all the modular batteries are connected in series with output 410. Thus, all of the batteries are connected is series. The output voltage at 410 for circuit 305 (FIG. 5) is four times that of the voltage of the single battery BAT2 at 510 (assuming the voltage of the batteries in modules 1000, 1100 and 1200 are the same and equal to BAT2 at 510 otherwise Equation (ii) applies. While three modules 1000, 1100, and 1200 are shown in circuit 305 it should be understood that the number of modules can be any number to achieve a desired voltage output at 410.

The invention being thus described, it will be evident that the same may be varied in many ways by a routineer in the applicable arts. Such variations are not to be regarded as a departure from the spirit and scope of the invention.

What is claimed is:

1. A circuit for generating a voltage surge from two or more low voltage sources, comprising:
   a non-module battery;
   a plurality of modules, each module
      comprising at least one module battery and one respective module circuit, wherein the module circuit is configured to accept control inputs to put the module battery in either a charging state or a discharging state by closing or opening, respectively, a path to ground from the negative terminal of the module battery, and wherein the module circuit does not affect a path to ground from the negative terminal of the non-module battery, and further wherein
      the plurality of modules and non-module battery are arranged to receive a charging current in parallel, and are further arranged to discharge a discharging current in series upon operation of the respective circuits;
   a controller configured to generate a control signal to operate the respective plurality of circuits to switch the non-module battery and plurality of module batteries between a charging state in which charging current is received in parallel, and a discharging state in which discharging current is provided in series; and
   an output configured to provide the discharging current, and wherein each of the respective module circuits comprise—
      a module circuit input connected to a first end of a first resistor, a first diode attached at an anode end to a source of charging current and at a cathode end to a positive terminal of the module battery, a first transistor comprising a first transistor gate connected to the control signal, a first transistor source connected to ground, and a first transistor drain connected to a second end of the first resistor, a second transistor comprising a second transistor gate connected to the second end of the first resistor and the first transistor drain, a second transistor source connected to ground, and a second transistor drain connected to a negative terminal of the module battery, a third transistor comprising a third transistor gate connected to the second end of the first resistor and the first transistor drain, a third transistor source connected to the module circuit input, and a third transistor drain connected to both the second transistor drain and negative terminal of the module battery, and a module circuit output connected to the cathode end of the first diode and positive terminal of the module battery.

2. The circuit according to claim 1 further comprising:

a charger configured to provide the charging current to each of the plurality of module batteries and non-module battery.

3. The circuit according to claim 1, further comprising:

a second diode connected in series between the charging source and the positive terminal of the non-modular battery, wherein the second diode is connected to allow charging current to flow from the charging source to the positive terminal of the non-modular batteries, and to prevent discharge current from the non-modular battery from charging the charging source.

\* \* \* \* \*